United States Patent [19]

Clarke et al.

[11] Patent Number: 4,907,888
[45] Date of Patent: Mar. 13, 1990

[54] NON DESTRUCTIVE TESTING AND OTHER APPLICATIONS USING RETROREFLECTIVE ILLUMINATION

[75] Inventors: Donald A. Clarke; Rodger L. Reynolds, both of Windsor; Timothy R. Pryor, Tecumseh, all of Canada

[73] Assignee: Diffracto Ltd., Windsor, Canada

[21] Appl. No.: 134,213

[22] Filed: Dec. 16, 1987

Related U.S. Application Data

[60] Continuation-in-part of Ser. No. 33,930, Apr. 2, 1987, Pat. No. 4,862,268, Continuation of Ser. No. 711,646, Mar. 14, 1985, abandoned, and a continuation-in-part of Ser. No. 933,851, Nov. 24, 1986, abandoned, which is a division of Ser. No. 579,971, Feb. 14, 1984, Pat. No. 4,629,319.

[51] Int. Cl.$^4$ ............................................. G01B 11/30
[52] U.S. Cl. .................................................... 356/371
[58] Field of Search ............... 356/237, 445, 129, 371; 73/605, 655

[56] References Cited

U.S. PATENT DOCUMENTS

| | | | |
|---|---|---|---|
| 3,667,846 | 6/1972 | Nater et al. | 356/445 |
| 3,734,626 | 5/1973 | Roberts et al. | 356/237 |
| 3,767,306 | 10/1973 | Mast et al. | 356/129 |
| 3,879,989 | 4/1975 | Brenden | 73/605 |
| 3,892,494 | 7/1975 | Baker et al. | 356/237 |
| 4,207,467 | 6/1980 | Doyle | 356/382 |
| 4,512,183 | 4/1985 | Alexander | 356/445 |
| 4,567,769 | 2/1986 | Barkhoudarian | 73/655 |
| 4,581,939 | 4/1986 | Takahashi | 73/655 |
| 4,629,319 | 12/1986 | Clarke et al. | 356/446 |

FOREIGN PATENT DOCUMENTS

85/03776  8/1985  PCT Int'l Appl. .................. 356/445

OTHER PUBLICATIONS

Sellin, R. H. J., "A Technique Based on the Schlieren Principle for Studying the Free Surface of a Liquid", Journal & Scientific Instruments, vol. 40, No. 7 (Jul. 1963), pp.355-357.

Primary Examiner—Richard A. Rosenberger
Attorney, Agent, or Firm—Larson and Taylor

[57] ABSTRACT

The invention concerns optical non-destructive test of materials using surface distortions detected by light which is reflected from the surface, retroreflected back to the surface and thence to form an image containing a greatly enhanced view of local deformation. In addition, the method is usable for determining surface characteristics of membranes and the like which can be influenced by sound and other wave energy from tested members and other sources and objects.

3 Claims, 2 Drawing Sheets

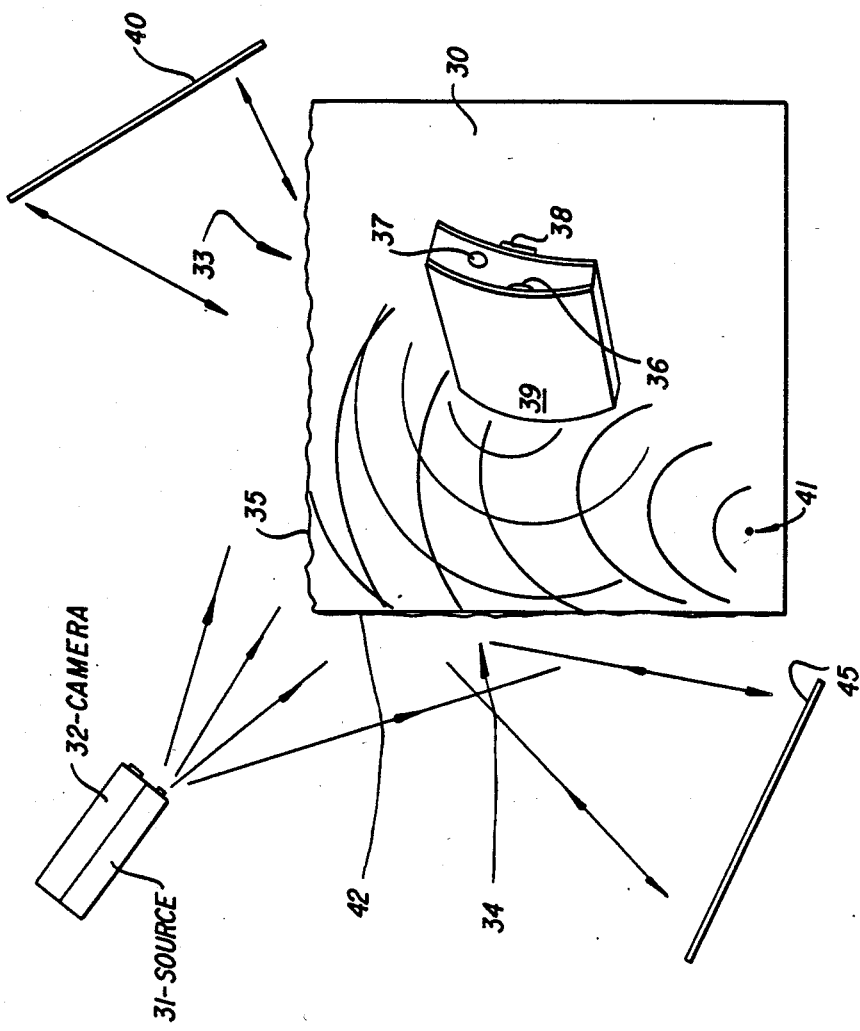

NON DESTRUCTIVE TESTING AND OTHER APPLICATIONS USING RETROREFLECTIVE ILLUMINATION

This application is a continuation in part of our co-pending application Ser. No. 07/033,930, filed Apr. 2, 1987, now U.S. Pat. No. 4,863,268 which is a continuation of Ser. No. 06/711,646, filed Mar. 14, 1985, now abandoned, entitled "Diffractosight Improvements" and Ser. No. 06/933,851, filed Nov. 24, 1986, now abandoned, which is a divisional of Ser. No. 06/579971, now U.S. Pat. No. 4,629,319 entitled "Panel Surface Flaw Inspection".

These applications describe a novel optical technique for magnifying surface deformation in an intelligible manner while leaving the rest of the image of the surface more or less untouched. This is especially novel for large surfaces, in excess of 2m extension say, which are very difficult, if not impossible to accurately monitor at high resolution using conventional means.

In the course of our work we have come to realize that the technique disclosed has numerous applications beyond those stressed in our previous disclosures. In particular it is now felt to be quite useful for detecting faults in materials, electromagnetic or thermal phenomena, and for detecting wave motion, for example, seismic waves on the earth, sound waves in water or air, etc. Such wave detection can be direct, from the surface of the medium in question, or via a suitable membrane which is responsive to the waves.

PRIOR ART

Numerous defects in materials and assemblies can be determined from distortion in the surface thereof. Previous optical non destructive testing methods for this purpose have desireably offered full field inspection via holographic fringe projection and Moire effects.

Substantial sensitivity is often required (e.g. under 10 micrometers) in surface deflection. Of the prior art above, holography has by far the most sensitivity. However, it is not widely used because of several disadvantages. It requires a coherent light source, some special medium must be used to store the results (e.g. superresolution film), a "before" and "after" picture is necessary and the object size is limited by the power of the coherent light source which cannot illuminate large volumes. In addition, severe registration limitations are required for the camera and the part between the before and after exposures. It is also difficult to view the results directly in real time particularly if the examination must be made with room lighting conditions and it is an expensive exercise both to purchase and to train the personnel to use it.

Finally, in many cases, holography can be too sensitive, with data provided complicated by extreme numbers of fringes.

Grid projection and Moire methods are far easier to use and cheaper to purchase, however they generally lack the sensitivity desired for most applications. Both these methods usually monitor displacement normal to the surface in question.

The invention disclosed herein is in many ways revolutionary. It approaches the sensitivity of holography but is quite simple and inexpensive. It requires little training in its application since it represents distortions in the surface of an object in a way similar to how the human normally would see similar distortions (albeit of much larger magnitude) on the same surface. It also has excellent sensitivity and measures the local distortion of the surface and can be viewed by the human or TV camera in room light conditions.

BRIEF DESCRIPTION OF THE DRAWINGS

FIG. 3 is a schematic elevation view of the imaging of surfaces of a fluid to determine surface variations caused by the excitation of an object in the fluid according to the present invention.

DETAILED DESCRIPTION OF THE PREFERRED EMBODIMENTS

Figure 1:
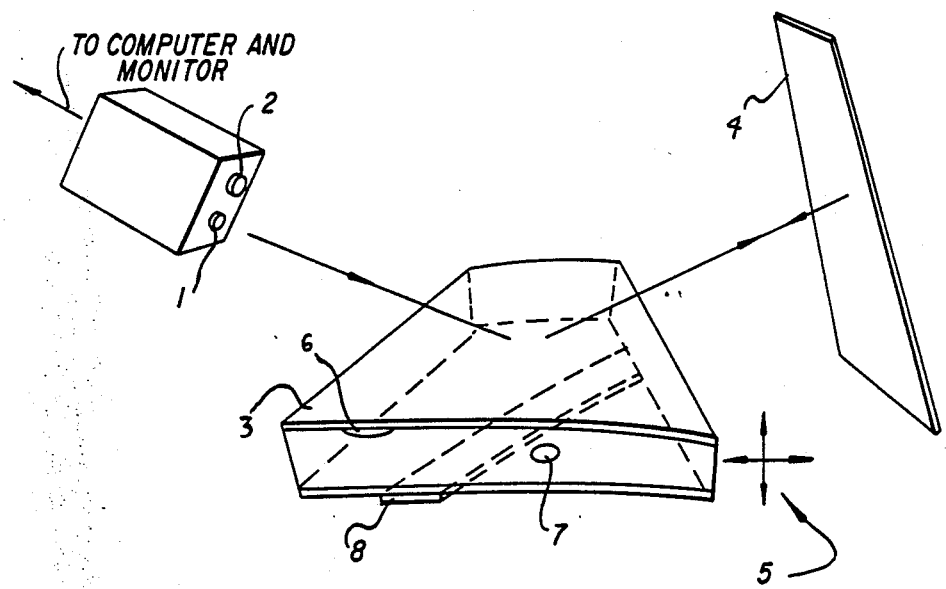
FIG. 1 is a schematic perspective view of the imaging of a surface of an object to determine defects beneath the surface according to the present invention.

FIG. 1 shows object, 3, under test, the surface of which is reflective at the optical wave length used or can be made so by the addition of a thin coat of oil, paint, etc. if necessary. Longer wave length sources (e.g. IR) are also possible if the surface is not naturally reflective.

Source 1 is typically a divergent source of radiation which illuminates the entire surface of object 3. This illumination reflects off of object 3 to the retroscreen 4 where it is redirected back towards the source on substantially the same path and imaged at the camera 2 as described in our U.S. Pat. No. 4,629,319 and referenced copending application.

If object 3 represents an airplane wing under test, then the image can be viewed directly, e.g. to determine stretching near rivet holes, or it can be compared to an image which existed previously so that any subsequent anomolies can be determined.

This can be visually determined or computer processing used, for example, subtracting out the normally appearing (e.g. unchanged) conditions and hence displaying only those areas which have deformed. Such image processing applications are further described in our co-pending application.

Excitation 5, via transducer or other excitation source not shown, may be mechanical, thermal, acoustic or of some other type, and may be periodic or transient. This excitation typically causes normal or in-plane amplitudes or resonances to occur in the surface of object 3. The resulting mode shapes and surface signatures will be detected at the camera 2, which may need to be strobed or operated at a high frame rate to capture the data (2000 frames/sec. video cameras are available from Spin Physics Division of Kodak Co. for example. The light source can also be strobed as well or in addition.

A delamination 6, or flaw 7 in the test object, or stiffener 8 attached for example to the bottom side, will distort the top surface of the object 3 during manufacture. This distortion will be detected at the camera as described in the references. Delamination 6, flaw 7 or stiffener 8, in the presence of excitation 5, will themselves modulate the resulting mode shapes and surface signatures in object 3 and this modulation will be detectable at the camera 2.

The camera and light source are here shown on a unitary housing but can be separate. A Cohu brand high resolution solid state TV camera and a 25 Watt halogen light bulb are good examples, however, film cameras with flash guns, and even the human eye and a flashlight can be used.

The retroreflective screen 4, can be desireably constructed using 3M Scotchlight type 7615 and can be flat or curved, and is positioned to be approximately perpendicular to the light from the surface. Other retroreflective elements including sprayed-on glass bead paint can also be employed.

The surface, camera/light source and screen can each or all be in relative motion relative to the other elements. There is no requirement to keep the camera/light and screen in fixed position. However, sensitivity can change with angle or distance, and needs to be accounted for.

Figure 2:
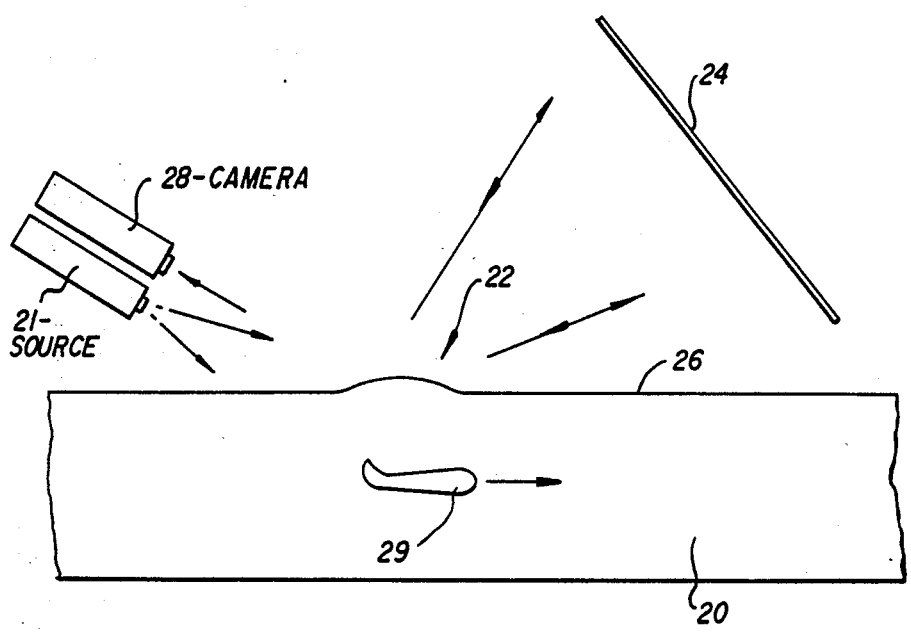
FIG. 2 is a schematic elevation view of the imaging of a surface of a fluid to determine the presence of characteristic of a moving object beneath the surface according to the present invention.

FIG. 2 shows (in somewhat exagerated form) the surface wave 22 which results from model 29 (or even a full size actual object) which is driven or towed on or under the surface of fluid 20. Detection of the surface variations is achieved with illumination source 21, retroreflector 24 and camera 20.

This inspection allows either the detection of such an event or a measure of this disturbance which in turn is proportional to the aerodynamic efficiency, or presence thereof. Presence detection indeed is valuable in submarine detection, determining bullet location in rifle barrels, etc.

The light sources herein are shown located somewhat spaced from the axis of the camera optics used to image the surface, with typical spacing being 0.1 to 1 degree. This arrangement gives a desirable light/dark "contour" presentation of the surface deformation. However, an on-axis arrangement using a beam splitter or other means to put the source effectively on the camera optical axis can also be used to identify where anomolies occur, and their magnitude, but without as good a feeling for their shape.

The light source width can range from point sources to much broader sources, e.g. $10 \times 10$ cm (where $3 \times 3$ m surfaces are illuminated). The choice of light source depends on the degree of fine detail desired in the image and the degree of surface slope variation expected. Generally, the larger sources give the most realistic image when larger slopes occur, whereas the point source provides the most sensitivity. Sensitivity indeed has been measured to 1 micron, when observing a 2 mm dia "bump" on a 2 meter square surface.

FIG. 3 shows a coherent source 41, typically ultrasonic, producing for illustration purposes, a hologram, 33, of the object 39, on the free surface 35 of the fluid 30. Alternatively, a hologram can be produced on the flexible membrane 42, also monitored according to the invention, using retroreflector 45. Each can be detected separately or in a combined apparatus as shown. It can be desireable to pressurize the air on the side of the membrane to offset the constant water pressure effect. A second coherent ultrasound source may be desireable to radiate through the object or illuminate the fluid surface or membrane.

The fluid surface variations are detected as described herein and in the references, using source 31, camera 32, and retroreflector 40.

This inspection can be used to determine the characteristics of the object, its orientation, presence of, and if the correct object is in fact present. It may also be used to determine subsurface errors or additions to the object such as delamination 36, flaw 37 or stiffener 38.

A similar test can be done in air using speakers to excite the part or membrane.

While generation of holograms have been shown, due to the coherent waves beating on the fluid or membrane surface, it is not necessary to produce same to use the invention. One can for example, use the invention to monitor any water or liquid wave patterns and their movements. Membrane or other surface distortions from any cause can also be monitored.

Wave sources can be acoustic, electromagnetic, thermal or any other suitable means. Electron beams or laser beams can also be used to create local thermal distortion in thermoplastic surfaces in response to input signals to the generator thereat, as a means of converting such energy to desireable surface distortion.

A suitable retroreflector is composed of a large number of closely spaced retroreflective elements. Light as defined can be any wave length desired from UV to IR even longer wavelengths can be used if suitable retroreflective material is available.

Processing of data sensed from the surface can be done by a variety of optical or digital means, many of which have been discussed in our co-pending application. Image subtraction is useful to illustrate before and after differences in surface condition, with or without excitation, etc.

A major application of the invention is thought to exist in the monitoring of car bodies, aircraft or other large structures on shaker tables. These objects have large, critical surfaces (sides, wings, etc.) which are very amenable to monitoring with the invention to determine resonances, made shapes, weaknesses and other data.

What is claimed is:

1. A method of detecting the presence of an object located below a surface of a liquid comprising the steps of:

moving one of the object and liquid relative to the other;

illuminating the surface with light;

retroreflecting the light from the surface back to the surface;

detecting the retroreflected light from the surface to determine the shape of the surface; and determining the presence of a surface variation in the shape of the surface which surface variation is thus indicative of the presence of the object below the surface.

2. A method of detecting the presence of an object as claimed in claim 1 wherein the determining step includes the steps of generating an image of the surface and comparing of the image with an image previously generated in the same manner.

3. A method of detecting the presence of an object as claimed in claim 1 and further including the step of determining the location of any surface variation.

* * * * *